United States Patent
Feldman et al.

(10) Patent No.: US 10,512,482 B2
(45) Date of Patent: Dec. 24, 2019

(54) SYSTEM AND METHOD FOR SCORING THE LEFT VENTRICULAR ENDOCARDIUM TO INCREASE LEFT VENTRICULAR COMPLIANCE

(71) Applicant: The Board of Regents of the University of Texas System, Austin, TX (US)

(72) Inventors: Marc D. Feldman, San Antonio, TX (US); Daniel Escobedo, San Antonio, TX (US); David L. Halaney, San Antonio, TX (US); Jordan C. Dwelle, San Antonio, TX (US); Austin B. McElroy, San Antonio, TX (US); Thomas E. Milner, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 548 days.

(21) Appl. No.: 14/433,763

(22) PCT Filed: Oct. 7, 2013

(86) PCT No.: PCT/US2013/063701
§ 371 (c)(1),
(2) Date: Apr. 6, 2015

(87) PCT Pub. No.: WO2014/055981
PCT Pub. Date: Apr. 10, 2014

(65) Prior Publication Data
US 2015/0265304 A1    Sep. 24, 2015

Related U.S. Application Data

(60) Provisional application No. 61/756,280, filed on Jan. 24, 2013, provisional application No. 61/710,183, filed on Oct. 5, 2012.

(51) Int. Cl.
A61B 17/32    (2006.01)
A61B 17/295    (2006.01)
(Continued)

(52) U.S. Cl.
CPC ........... *A61B 17/320016* (2013.01); *A61B 17/00234* (2013.01); *A61B 17/295* (2013.01);
(Continued)

(58) Field of Classification Search
CPC ...... A61B 17/320016; A61B 17/00234; A61B 17/295; A61B 17/320725; A61B 2017/00243
See application file for complete search history.

(56) References Cited

U.S. PATENT DOCUMENTS 5,195,956 A    3/1993    Stockmeier
5,295,958 A    3/1994    Shturman
(Continued)

FOREIGN PATENT DOCUMENTS

WO    95/15715    6/1995
WO    9635469    11/1996
(Continued)

OTHER PUBLICATIONS

International Search Report and Written Opinion for PCT/US2014/052903 dated Feb. 6, 2015.
(Continued)

*Primary Examiner* — Julie A Szpira
(74) *Attorney, Agent, or Firm* — Meyertons, Hood, Kivlin, Kowert & Goetzel, P.C.

(57) ABSTRACT

In some embodiments, a system for scoring human endocardium tissue may include a first conduit and an activation system. The first conduit may include a first opening, a second opening, and a cutting device. The first opening may be positioned at a proximal end of the first conduit. The
(Continued)

second opening may extend from adjacent to a closed distal end portion of the first conduit. The cutting device, when activated, may cut through a portion of a depth of endocardium tissue positioned adjacent the second opening. The cutting device may selectively cut or score the endocardium to a specified depth and length in the endocardium of a left ventricle of a human heart.

14 Claims, 14 Drawing Sheets

(51) Int. Cl.
| | | |
|---|---|---|
| *A61B 17/3209* | (2006.01) | |
| *A61B 17/00* | (2006.01) | |
| A61B 17/3207 | (2006.01) | |
| A61B 18/14 | (2006.01) | |
| A61B 17/22 | (2006.01) | |
| A61B 17/34 | (2006.01) | |
| A61B 18/24 | (2006.01) | |

(52) U.S. Cl.
CPC .. *A61B 17/3209* (2013.01); *A61B 17/320725* (2013.01); *A61B 18/14* (2013.01); *A61B 18/24* (2013.01); *A61B 2017/00243* (2013.01); *A61B 2017/00247* (2013.01); *A61B 2017/00876* (2013.01); *A61B 2017/22061* (2013.01); *A61B 2017/320052* (2013.01); *A61B 2017/3425* (2013.01)

(56) References Cited

U.S. PATENT DOCUMENTS

| | | | |
|---|---|---|---|
| 5,370,134 A | | 12/1994 | Chin et al. |
| 5,397,333 A | * | 3/1995 | Knoepfler ...... A61B 17/320016 606/167 |
| 5,655,548 A | | 8/1997 | Nelson et al. |
| 5,695,511 A | | 12/1997 | Cano et al. |
| 5,755,714 A | | 5/1998 | Murphy-Chutorian |
| 5,824,071 A | | 10/1998 | Nelson et al. |
| 5,855,614 A | | 1/1999 | Stevens et al. |
| 5,931,848 A | | 8/1999 | Saadat |
| 5,972,030 A | | 10/1999 | Garrison et al. |
| 6,051,008 A | | 4/2000 | Saadat et al. |
| 6,056,743 A | | 5/2000 | Ellis et al. |
| 6,080,175 A | | 6/2000 | Hogendijk |
| 6,125,852 A | | 10/2000 | Stevens et al. |
| 6,165,188 A | | 12/2000 | Saadat et al. |
| 6,251,104 B1 | * | 6/2001 | Kesten ............... A61B 18/24 604/158 |
| 6,254,621 B1 | | 7/2001 | Shackelford et al. |
| 6,387,108 B1 | | 5/2002 | Taylor et al. |
| 6,447,539 B1 | | 9/2002 | Nelson et al. |
| 6,514,248 B1 | | 2/2003 | Eggers et al. |
| 6,638,235 B2 | * | 10/2003 | Miller ............... A61B 10/025 600/564 |
| 6,681,773 B2 | | 1/2004 | Murphy et al. |
| 6,796,963 B2 | | 9/2004 | Carpenter et al. |
| 6,802,319 B2 | | 10/2004 | Stevens et al. |
| 6,899,704 B2 | | 5/2005 | Sterman et al. |
| 6,959,711 B2 | | 11/2005 | Murphy et al. |
| 7,101,402 B2 | | 9/2006 | Phelps et al. |
| 7,186,210 B2 | | 3/2007 | Feld et al. |
| 7,255,706 B2 | | 8/2007 | Rosengart |
| 7,335,158 B2 | | 2/2008 | Taylor |
| 7,470,272 B2 | | 12/2008 | Mulier et al. |
| 7,485,088 B2 | | 2/2009 | Murphy et al. |
| 7,485,090 B2 | | 2/2009 | Taylor |
| 7,513,867 B2 | | 4/2009 | Lichtenstein |
| 7,520,886 B2 | | 4/2009 | Surti |
| 7,608,091 B2 | | 10/2009 | Goldfarb et al. |
| 8,292,884 B2 | | 10/2012 | Levine et al. |
| 2002/0029783 A1 | | 3/2002 | Stevens et al. |
| 2002/0068924 A1 | | 6/2002 | Sinofsky |
| 2002/0193782 A1 | * | 12/2002 | Ellis ............... A61B 17/3207 606/15 |
| 2003/0102000 A1 | | 6/2003 | Stevens et al. |
| 2004/0002626 A1 | | 1/2004 | Feld et al. |
| 2004/0034380 A1 | | 2/2004 | Woolfson et al. |
| 2004/0193191 A1 | | 9/2004 | Starksen et al. |
| 2005/0197693 A1 | * | 9/2005 | Pai ............... A61B 17/00234 623/2.1 |
| 2005/0288654 A1 | | 12/2005 | Niemen et al. |
| 2006/0095025 A1 | | 4/2006 | Levine et al. |
| 2007/0010812 A1 | * | 1/2007 | Mittelstein ......... A61B 18/1482 606/48 |
| 2007/0073274 A1 | | 3/2007 | Chin et al. |
| 2008/0015466 A1 | * | 1/2008 | Lerman ............... A61B 10/06 600/567 |
| 2008/0234728 A1 | | 9/2008 | Starksen et al. |
| 2009/0069888 A1 | | 3/2009 | Drake |
| 2009/0149872 A1 | * | 6/2009 | Gross ............... A61F 2/2445 606/151 |
| 2009/0287143 A1 | | 11/2009 | Line |
| 2009/0306582 A1 | | 12/2009 | Granada et al. |
| 2011/0118769 A1 | | 5/2011 | Bliss et al. |
| 2012/0041500 A1 | | 2/2012 | Zhu et al. |
| 2013/0103047 A1 | * | 4/2013 | Steingisser ......... A61N 1/3756 606/129 |
| 2016/0213393 A1 | | 7/2016 | Feldman et al. |

FOREIGN PATENT DOCUMENTS

| | | |
|---|---|---|
| WO | 2011060386 | 5/2011 |
| WO | 2014055981 | 4/2014 |
| WO | 2015031476 | 3/2015 |

OTHER PUBLICATIONS

International Preliminary Report on Patentability for PCT/US2014/052903 dated Mar. 1, 2016.
International Preliminary Report on Patentability from PCT/US2013/063701, dated Apr. 16, 2015, Board of Regents, The University of Texas System, pp. 1-10.
Restriction for U.S. Appl. No. 14/915,394 dated Apr. 4, 2018.
Non Final Office Action for U.S. Appl. No. 14/915,394 dated Nov. 15, 2018.

* cited by examiner

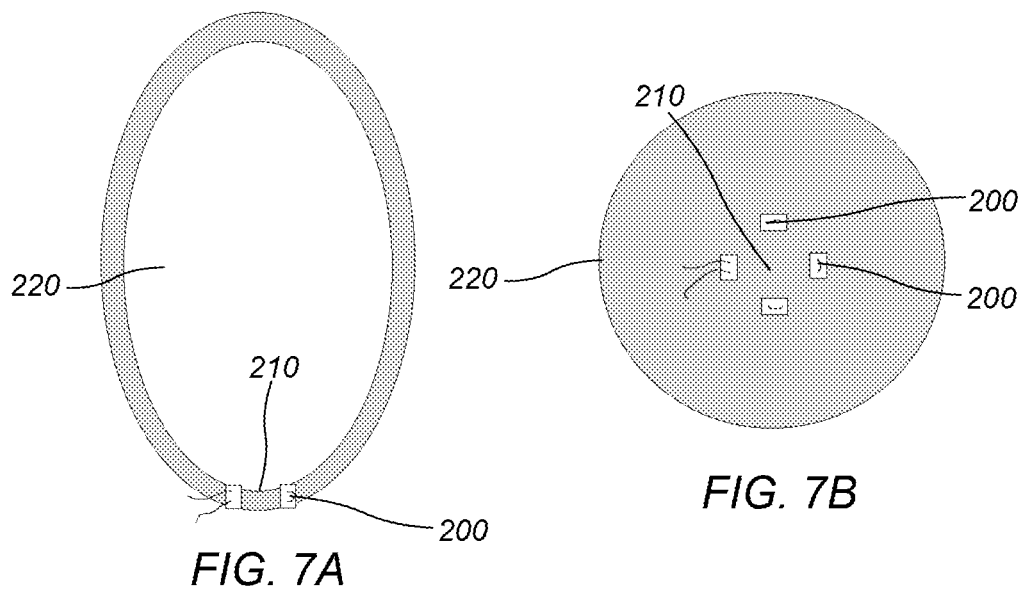
FIG. 7A
FIG. 7B
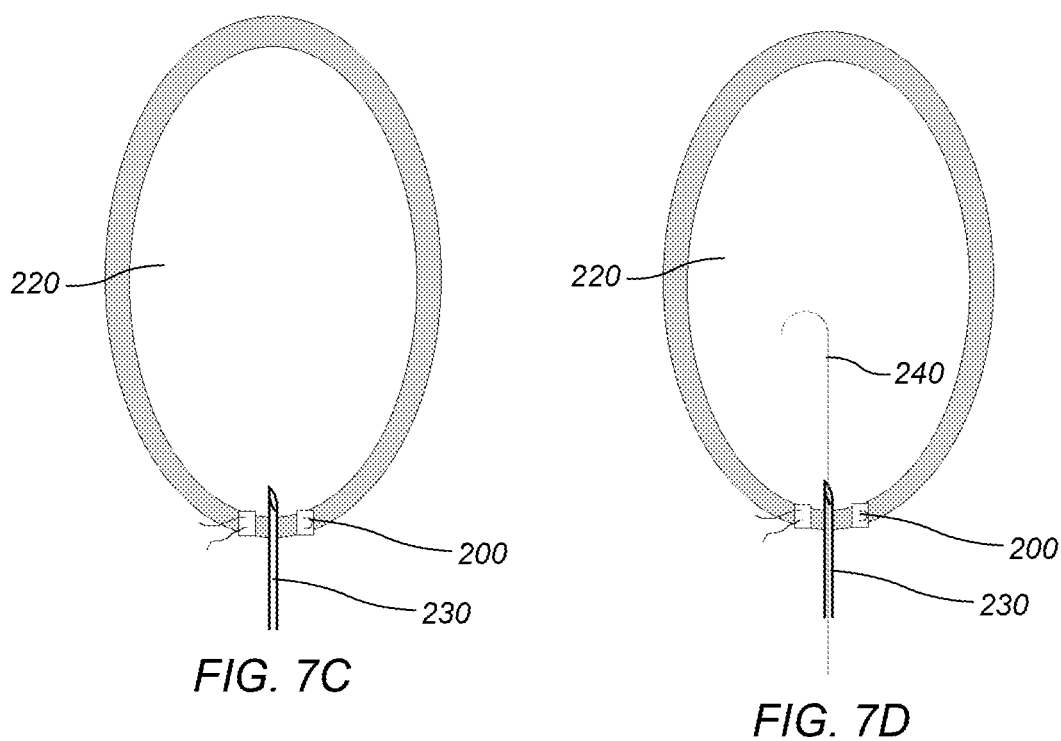
FIG. 7C
FIG. 7D

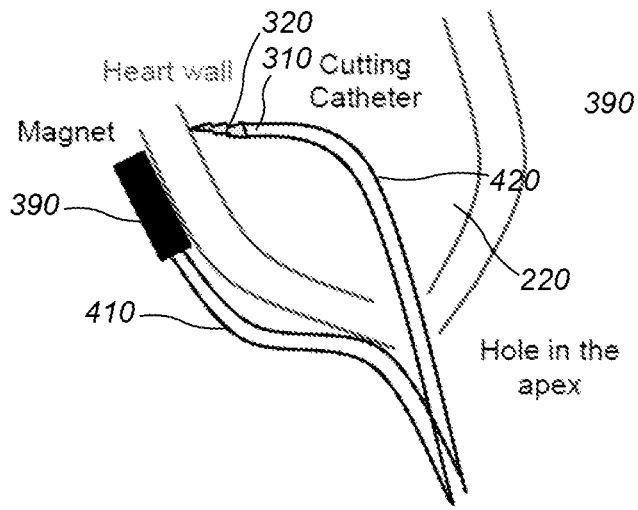
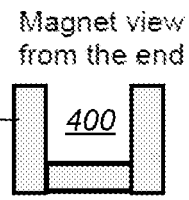
FIG. 15B
Channel helps keep blade centered and parallel. Cutting tissue without the magnet is a safety feature, as there would be little counter force for the cutting blade and cutting would be difficult.
FIG. 15A
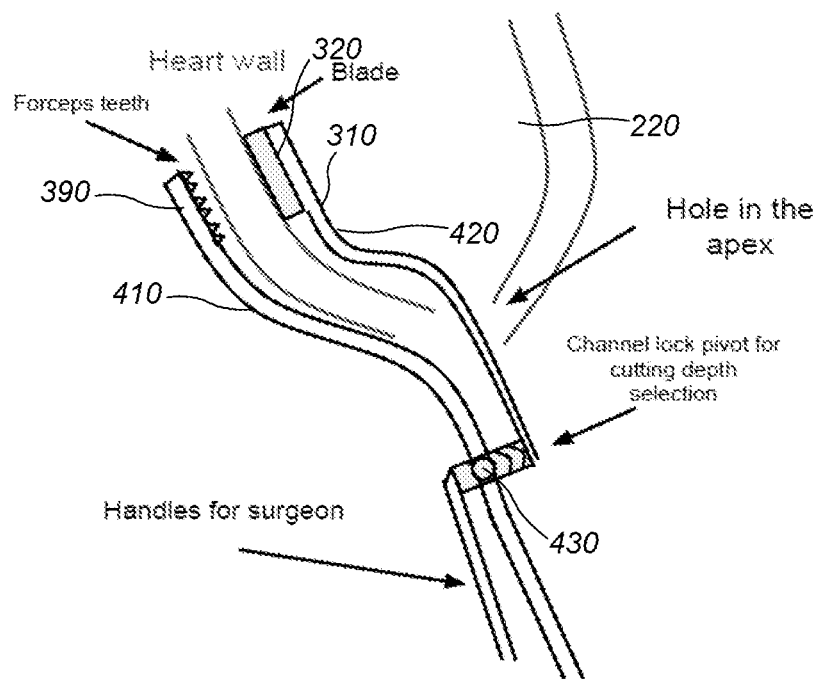
FIG. 16

SYSTEM AND METHOD FOR SCORING THE LEFT VENTRICULAR ENDOCARDIUM TO INCREASE LEFT VENTRICULAR COMPLIANCE

BACKGROUND OF THE INVENTION

1. Field of the Invention

The present disclosure generally relates to increasing left ventricular compliance. More particularly, the disclosure generally relates to systems and methods for scoring endocardium tissue.

2. Description of the Relevant Art

Left ventricular (LV) diastolic dysfunction (reduced compliance) was first identified in the 1970s as an important etiology producing shortness of breath in patients at rest and exertion, and as a major cause of hospital admission due to diastolic heart failure. Half of all heart failure admissions are due to left ventricular systolic failure (enlarged weak hearts), but half are caused by hearts with normal systolic function that are thickened with diastolic dysfunction. Despite 40 years developing solutions to improve left ventricular diastolic compliance, there have been no mediations or therapies invented which can acutely and permanently increase compliance. Medications which reduce calcium availability to the myocytes have not successfully improved diastolic compliance. As a result, medications are being used to slow the heart rate to prolong diastole (calcium and beta blockers), or decrease left ventricular filling pressures by moving down a fixed compliance curve with diuretics to reduce blood volume. However, there are no medications which can improve left ventricular diastolic compliance. That is because left ventricular compliance is known to be primarily related to the thickness of the left ventricular myocardium (normally 8-9 mm and increases to 12-16 mm) and the increase in the percentage of fibrosis which is known to occur as left ventricular hypertrophy develops (3% up to 12%). A genetic heart muscle condition called hypertrophic cardiomyopathy exists wherein a patient's heart can be as thick as 40 mm and the percentage of fibrosis can exceed more than 20% of the mass of the left ventricle.

The only therapeutic intervention currently available is the use of pharmacologicals to lower blood pressure in cases of left ventricular hypertrophy due to hypertension. However, although left ventricular hypertrophy can regress over months of time with normalization of blood pressure, left ventricular hypertrophy often cannot be completely normalized and often results in an increase in the percentage of fibrosis of the myocardium. Many other etiologies for left ventricular hypertrophy besides hypertension are recognized including diabetes, valvular heart disease, and hypertrophic cardiomyopathy. The relevant patient population is very large both in the U.S. (millions), and around the world.

U.S. Pat. No. 6,165,188 issued to Saadat et al. (hereinafter "Saadat") discloses an apparatus and methods for percutaneously performing myocardial revascularization using a catheter having an end region that is directable to contact a patient's endocardium at a plurality of positions. However, Saadat does not disclose a cutting device which is conveyed along a guide system in a first conduit to score endocardium tissue. Although there exist many different types of surgical devices none of the known devices accomplish what the herein described scoring device is capable of.

Therefore a system and/or method which results in increase in left ventricular compliance is highly beneficial.

SUMMARY

This disclosure describes systems and methods for, in some embodiments, scoring human endocardium tissue wherein the system may include a first conduit and an activation system. The first conduit may include a first opening, a second elongated opening, a cutting device, a guide system, and/or a shaping member. The first opening may be positioned at a proximal end of the first conduit extending through the proximal end in communication with a first lumen extending through the first conduit. The second elongated opening may extend from adjacent to a closed distal end of the first conduit along a distal portion of the first conduit. The cutting device may be positioned in the distal portion of the first conduit. The cutting device, when activated, may cut, during use, through at least a portion of a depth of endocardium tissue positioned adjacent the second elongated opening.

In some embodiments, the guide system may be positioned adjacent to the second elongated opening. In some embodiments, the cutting device may be coupled to the guide system such that the cutting device is conveyed along the second elongated opening when activated during use. The shaping member may be coupled along a distal portion of the first conduit. The shaping member, when activated during use, may change from a first shape to a second shape. The first shape may be substantially straight. The second shape may substantially conform to a portion of an interior perimeter or endocardium of a left ventricle. The activation system may activate the cutting device.

In some embodiments, a system may include a stabilizing device for applying, during use, a substantially opposing force on the epicardium substantially opposite the cutting device when the cutting device cuts through at least a portion of the depth of the endocardium tissue.

In some embodiments, the cutting device may be positionable in the first conduit. The cutting device may be configurable to assume a first shape and a second shape. The first shape may facilitate movement of the cutting device through the first conduit and the second shape is substantially equivalent to an interior of a left ventricle or a sphere or spheroid. When the cutting device assumes the second shape in a left ventricle the cutting device cuts, during use, through at least a portion of a depth of endocardium tissue positioned adjacent the cutting device.

In some embodiments, a method of ameliorating diastolic dysfunction may include positioning a second conduit in a human body such that a distal end of the second conduit is positioned in a left ventricle of a human heart. The method may include positioning a first conduit in the second conduit such that a distal end of the first conduit extends beyond the distal end of the second conduit into the left ventricle. The method may include activating a cutting device to sever at least one trabeculae carneae. Severing trabeculae carneae in a left ventricle of a human heart may release elastic forces on the left ventricle. At least some of the trabeculae carneae may be severed adjacent an apex of the left ventricle.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 7A-H depict a diagram of a side view of an embodiment of a method for preparing a pathway through the apex of a left ventricle for an instrument for scoring human endocardium tissue in a left ventricle.

FIGS. 15A-B depict a diagram of a side view of an embodiment of a system for scoring human endocardium tissue in a left ventricle after insertion of a distal end of the system in the left ventricle, wherein the system may include a magnet which assists in guiding a blade during the scoring of the endocardium tissue.

FIG. 16 depicts a diagram of a side view of an embodiment of a system for scoring human endocardium tissue in a left ventricle after insertion of a distal end of the system in the left ventricle, wherein the system may include a substantially fixed forceps which assists in guiding a blade during the scoring of the endocardium tissue.

Figure 1:
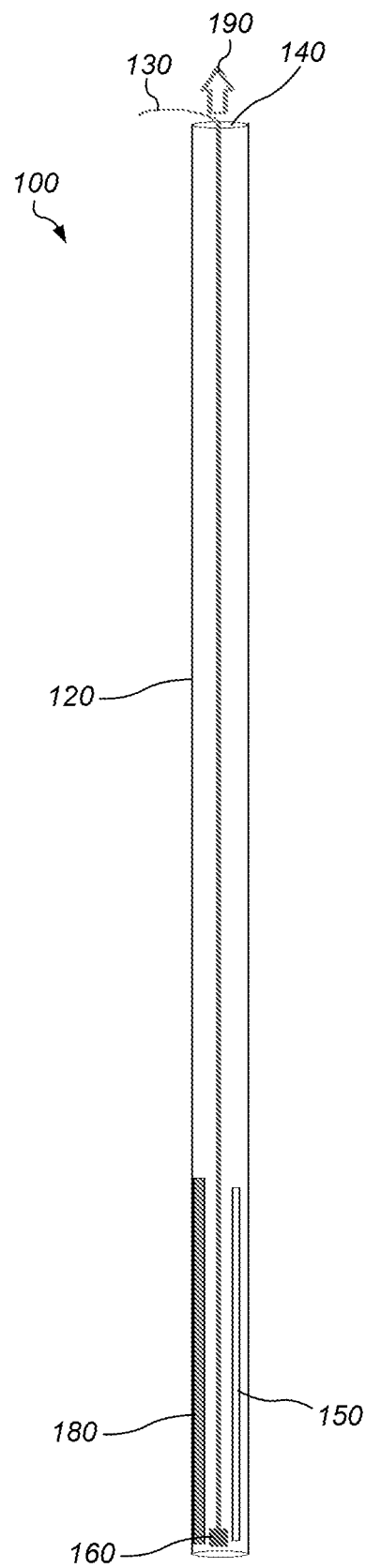
FIG. 1 depicts a diagram of a side view of an embodiment of a system for scoring human endocardium tissue.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112, paragraph six, interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "score" as used herein generally refers to precisely cutting a thin line along the longitudinal axis of the left ventricle (apex to base) of variable depth and/or variable length causing minimal damage to the endocardium.

This disclosure describes systems and methods for scoring endocardium tissue which results in increase in left ventricular compliance. In some embodiments, scoring a left ventricular endocardium may increase left ventricular compliance, improve patient symptoms and reduce hospital admissions due to diastolic dysfunction and heart failure. Scoring the left ventricular endocardium may be accomplished with longitudinal cuts (e.g., from about the apex to about the base) in the endocardium. The cuts may be made such that only a portion of the depth is pierced such that an opening in the left ventricle is not created.

In some embodiments, endocardium of the left ventricle may be accessed via the aortic valve during open heart surgery. In other embodiments, endocardium of the left ventricle may be accessed through the mitral valve. In other embodiments, endocardium of the left ventricle may be accessed by piercing the apex of the left ventricle. In some embodiments, the endocardium may be scored by taking a razor blade and cutting the endocardium at a variable length along the longitudinal axis (i.e., apex to base). Scoring the endocardium may be performed in the cardiac catheterization laboratory from the femoral, radial or brachial arteries to reduce the morbidity and mortality to the patient. A catheter may be passed through the peripheral artery and placed across the aortic value at the base of the heart. Through this catheter it is proposed to pass a preformed catheter (e.g., made of nitinol) that will allow laying a long catheter with one side (longitudinal side or opening along the length of the device) opened which can apply vacuum to the endocardium to attach the catheter from apex to base. The layer of endocardium which has been vacuum-attached into the longitudinal catheter may then be cut or scored. Methods to score the endocardium may include a longitudinal razor blade or scalpel which will cut only the layer of endocardium held within the catheter for patient safety. In some embodiments, a method to cut the endocardium may include a laser. The laser may be capable to both cut the myocardium in a controlled fashion as an alternative to razors and scalpels, but in addition has the capability of allowing myocardial and fibrous tissue healing in a more advantageous manner.

There is concern that the endocardium cuts may heal over weeks of time and the acute improvement in diastolic compliance will be lost as a result. To minimize this possibility, we may perform our primary cut with razor blade or scalpel and perform a second laser treatment of the endocardium. In some embodiments, the primary cut may be performed with a laser. The value of the laser is that the cut by the razor blade or scalpel may create frayed edges to the myocardium and collagen fibers which may make it more likely that the cut edges will locate each other and heal. It is also anticipated that new collagen growth along the endocardium cut may occur allowing the heart to reverse its acute gain in diastolic compliance resulting from the procedure. The laser therapy may seal the frayed edges of myocardial and fibrous tissue, making it less likely that the acute gain in compliance will be lost with time. In some embodiments, it is anticipated that the cutting device may deposit a medication along the length of the longitudinal cut to inhibit the healing process to minimize healing of these cuts. These medications could include anti-inflammatory, anti-fibrotic, or medications to minimize tissue healing processes. In some embodiments, radio frequency ablation may be employed to minimize healing of the scores or cuts to the endocardium tissue. In some embodiments, two blades may be used to remove a wedge-shaped piece of endocardium tissue rather than produce a narrow score to mitigate healing of the cuts to the endocardium tissue.

The optimal number of cuts to the endocardium may vary. In some embodiments, the number of cuts to the endocardium may vary from 1, 2, 3, 4, 5, 6, 7, or 8 cuts. The depth to which the endocardium is scored may also vary depending upon the subject's needs. In some embodiments, the endocardium may be scored to a depth of about 20-80%, 30-70% or 40-60% of the left ventricle wall thickness. There is safety to cutting the endocardium since the blood supply to the myocardium is derived from the other side (epicardium). Further, there is precedence for cuts in the endocardium in nature. For example, reptilian hearts have vast endocardium channels as a method to provide oxygen and nutrients to the endocardium.

The approach described herein, where this procedure is performed in patients during cardiac catheterization, is consistent with current trends in cardiology and cardiothoracic surgery in that surgery is moving towards more noninvasive systems and methods. There are many examples over the last two decades of moving away from open procedures with an anterior thoracotomy and the heart arrested on bypass, which increase the morbidity and mortality to the patient. As a result, stents are used in place of bypass grafts, heart valves are replaced in the catheterization laboratory (TAVR) in the elderly rather than in the traditional operating room, and atherectomy is used to remove atherosclerotic plaque from peripheral arteries rather than perform more traditional reverse saphenous vein bypass.

In some embodiments, additional safety may be introduced when the procedure is performed in the catheterization laboratory by transiently pacing the heart at 180-200 bpm to arrest the heart for 3-4 seconds while scoring the endocardium. In some embodiments, additional safety may be introduced when the procedure is performed in the catheterization laboratory by using intra-cardiac echo (ICE) to visualize the location where the longitudinal vacuum device has been applied to the endocardium before razor or laser cuts are performed. In the case of the later, one does not want to cut or injury the papillary muscles which anchor the mitral value. The use of ICE (echo placed in the right ventricle) may provide a detailed image of the location of the longitudinal vacuum device before any endocardium is cut (e.g., with either a razor or a laser). If there is any concern with cutting the papillary muscle, the device can be safely repositioned. Regarding the former, placement of aortic valves during heart catheterizations (TAVR) uses the approach of rapid heart pacing to transiently minimize heart motion for several seconds, and the same technique may be applied to scoring the endocardium as described herein.

FIG. 1 depicts a diagram of a side view of an embodiment of a system 100 for scoring human endocardium tissue 110. In some embodiments, system 100 may include a first conduit 120 and an activation system 130.

In some embodiments, first conduit 120 may include a first opening 140, a second elongated opening 150 to which a vacuum will be applied to hold or attach the device to the endocardium, a cutting device 160, a guide system 170, and a shaping member 180. First opening 140 may be positioned at a proximal end of first conduit 120 extending through the proximal end in communication with a first lumen extending through the first conduit. Second elongated opening 150 may extend from adjacent to a closed distal end of first conduit 120 along a distal portion of the first conduit.

The first conduit may include a long thin tube (e.g., diameter=2-3 mm). The tube may have one end closed (bottom end in FIG. 1). On one side, near the closed distal end, there may be second elongated opening 150 (e.g., approximately 7-8 cm long) through which a vacuum pressure will be applied to hold or attach the device to the endocardium. Opposite the second elongated opening may be shaping member 180 (e.g. a nitinol backbone of approximately the same length as the second elongated opening). Resting near the closed end of the tube may be a mounted cutting device (e.g., a mounted razor or scalpel blade, or laser), attached to activation system 130 (e.g., a 'rip cord') which may be used to pull the mounted blade or laser along the tube. A pressure reduction system or vacuum applied to 190 may be attached to the other end of the tube, but not turned on. The shaping member assumes its final contour or shape once it is exposed to body or its activation temperature (e.g., 37° C.). The position of the conduit or device along the endocardium may be confirmed to not include either papillary muscle or chordae to prevent the creation of mitral regurgitation as a complication. The vacuum applied to 190 may be turned on to hold the catheter in place relative to the endocardium of the left ventricle. Now the activation system may be activated, moving the blade or laser along the elongated opening, and making an incision along the endocardium which is being pulled into the elongated opening.

Figure 5:
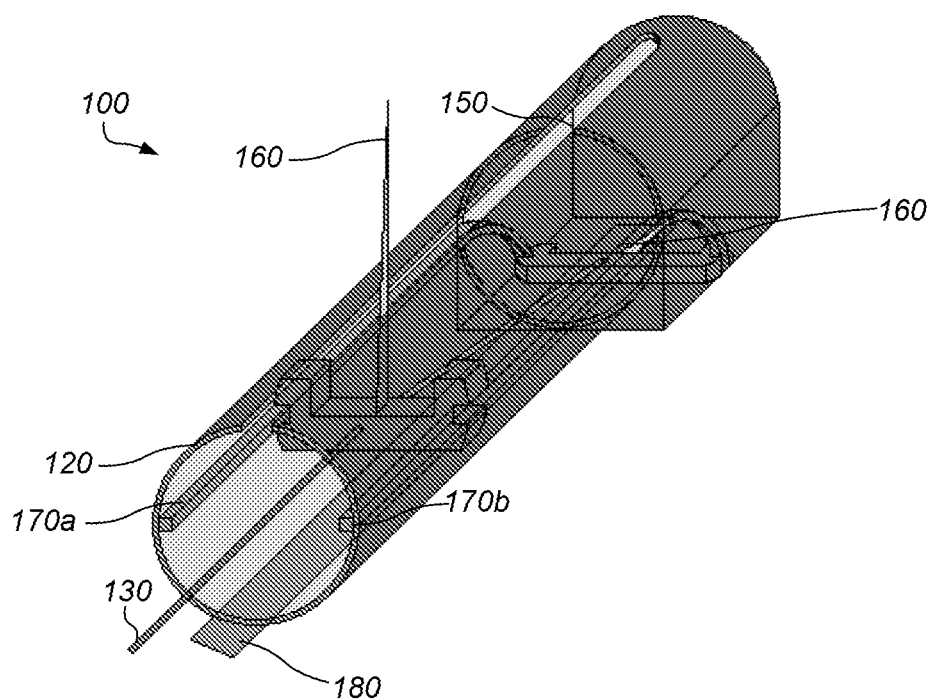
FIG. 5 depicts a diagram of a perspective view of an embodiment a distal portion of a cutting device, specifically a blade, moving along a guide system adjacent a second elongated opening in a distal portion of a first conduit.
Figure 6:
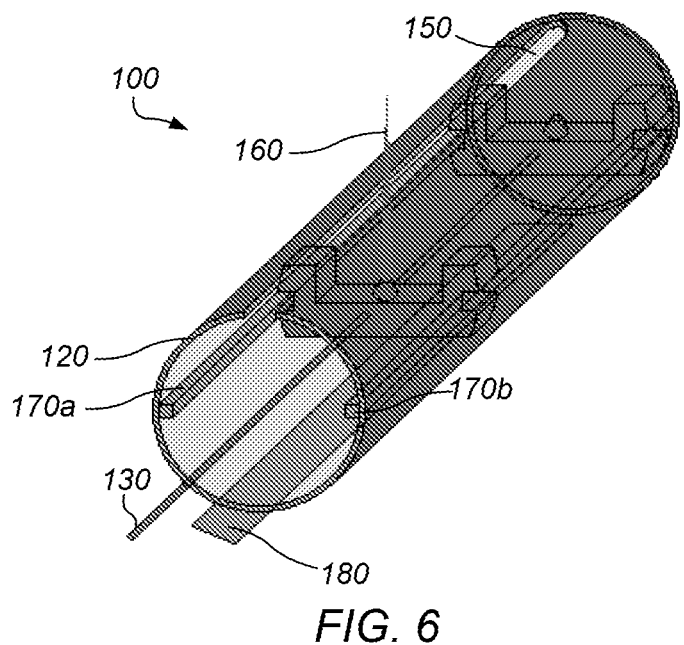
FIG. 6 depicts a diagram of a perspective view of an embodiment a distal portion of a cutting device, specifically a laser, moving along a guide system adjacent a second elongated opening in a distal portion of a first conduit.

Cutting device 160 may be positioned in the distal portion of the first conduit. In some embodiments, the cutting device, when activated, may cut, during use, through at least a portion of a depth of endocardium tissue positioned adjacent the second elongated opening. The cutting device may include a blade (e.g., as depicted in FIG. 5). Blades may include surgical blades such as scalpels, razor blades, etc. Blades may be formed from a variety of materials (e.g., metal, ceramic, plastic, etc.). In some embodiments, a cutting device may include a laser (e.g., as depicted in FIG. 6). In some embodiments, a cutting device may include two or more cutting devices, for example, wherein a first cutting device includes a blade and a second cutting device includes a laser. In some embodiments, two blades may cut simultaneously to remove a wedge-shaped piece of endocardium tissue (e.g., as depicted in FIG. 13A-F) instead of simply scoring the tissue.

Guide system 170 may be positioned adjacent the second elongated opening. The cutting device may be coupled to the guide system such that the cutting device is conveyed along the second elongated opening when activated during use. A guide system may include a first guide rail 170a coupled to an interior surface of a distal portion of the first conduit and a second guide rail 170b coupled to an interior surface of a distal portion of the first conduit substantially opposite to the first guide rail. The cutting device may be coupled such that the cutting device slides along the guide rails when activated. In some embodiments, for example when a cutting device includes a blade, the guide rails may curve downward (e.g., as depicted in FIG. 5) such that the blade is repositioned such that the blade is not exposed outside of the first conduit (i.e., so that the blade may not cut anything before activation). The rails may be curved at the beginning and/or end of the rails.

FIG. 5 shows an embodiment of a first conduit end if a blade is used to make the incision. The blade starts out in a recessed position inside the first conduit, which protects the blade and the patient while the first conduit is being inserted into the LV and positioned. Once the rip cord is pulled, the mounted blade is guided by guide rails, causing it to protrude through the second elongated opening and into the suctioned endocardium. At the end of the second elongated opening, a similar downward bend of the side-rails may allow for the blade to be recessed as the first conduit is removed. Once the incision is made, the catheter is released from the endocardium by removing the vacuum pressure.

FIG. 6 shows a preliminary design for a first conduit end if a laser is used to make the incision. In this case, no recession may be required, as the laser is not switched on until the endocardium is suctioned into place. The laser may cut alone, or may emit radiation following the blade to seal frayed ends of collagen and myocardial fibers, to inhibit the endocardial incision from re-sealing over time.

Figure 3:
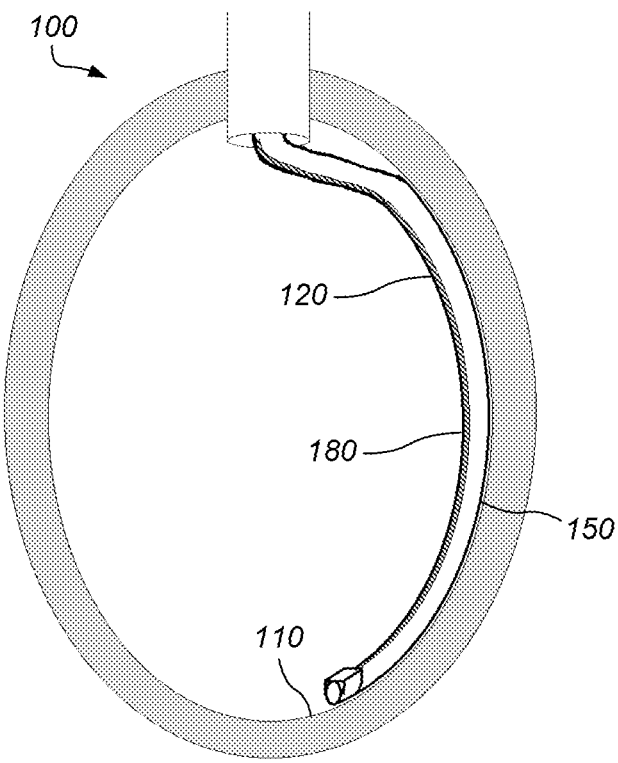
FIG. 3 depicts a diagram of a side view of an embodiment of a system for scoring human endocardium tissue in a left ventricle after activation of a shaping member associated with a distal portion of a first conduit.

The shaping member may be coupled along a distal portion of the first conduit. The shaping member, when activated during use, may change from a first shape to a second shape. The first shape may be substantially straight. The second shape may substantially conform to a portion of an interior perimeter or endocardium of a left ventricle. The shaping member may be activated by allowing the shaping member to warm up to a prespecified temperature (e.g., human body temperature). The shaping member may include a shape memory material. The shaping member may include nitinol. In some embodiments, upon entering the heart, the nitinol may warm to physiologic temperature (37° C.). This will cause the nitinol to assume a preformed shape which matches the contour of the side wall or endocardium of a human left ventricle (e.g., as depicted in FIG. 3). In some embodiments, an entire distal end of the first conduit may be formed from nitinol or even a majority or all of the first conduit may be formed from nitinol.

The activation system may activate the cutting device. In some embodiments, the activation system may include a wire coupled to the cutting device. When tension is applied to the wire, during use, the cutting device may be conveyed along a guide system from a distal end of the first conduit along the second elongated opening towards the proximal end of the first conduit. The wire may be flexible while still retaining some rigidity such that the wire may be used to move the cutting device from a proximal end of the first conduit along the second elongated opening towards the distal end of the first conduit. In some embodiments, the activation system may include a contact sensor that can provide a signal to initiate activation. The contact sensor may function to insure the cutting system is not activated until full contact is made. In addition, the activation system may function to disengage the cutting system if sufficient contact is not maintained.

Figure 4:
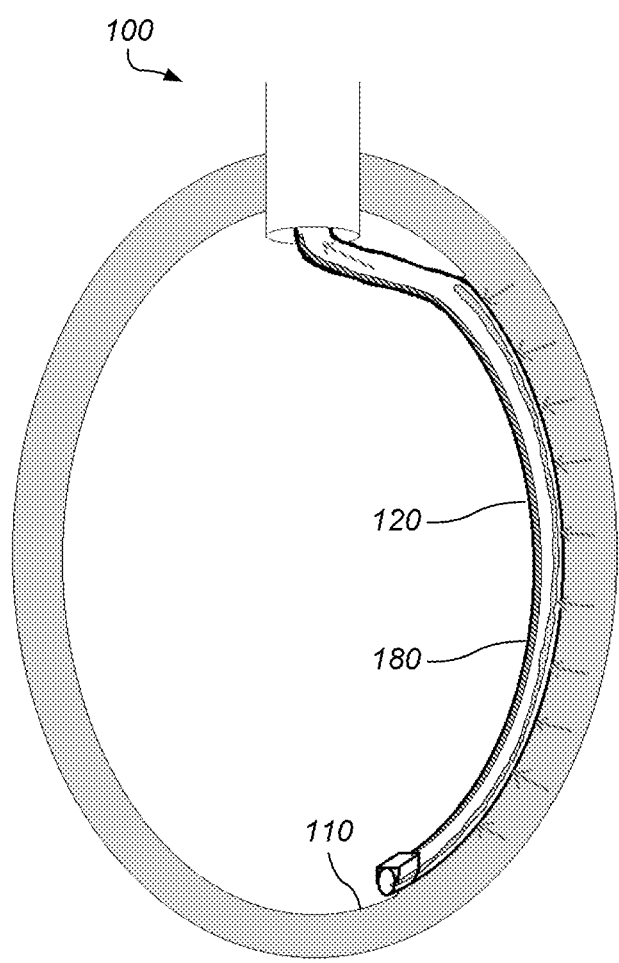
FIG. 4 depicts a diagram of a side view of an embodiment of a system for scoring human endocardium tissue in a left ventricle after decreasing pressure or creating a vacuum in a first conduit to inhibit movement of endocardial tissue relative to the first conduit.

In some embodiments, the system may include a pressure reducing system couplable or vacuum, during use, applied to the first opening of the first conduit. When the pressure reducing system is activated pressure may be reduced in the first conduit coupling endocardium tissue to the second elongated opening of the first conduit such that the endocardium tissue is inhibited from moving relative to the second elongated opening. Once the catheter has been positioned along the left ventricle wall (e.g., guided by angiography, or intra-cardiac echocardiography, ICE), the vacuum may be turned on, causing the endocardium of the left ventricle wall to be pulled into the second elongated opening and positioned there securely (e.g., as depicted in FIG. 4).

Figure 2:
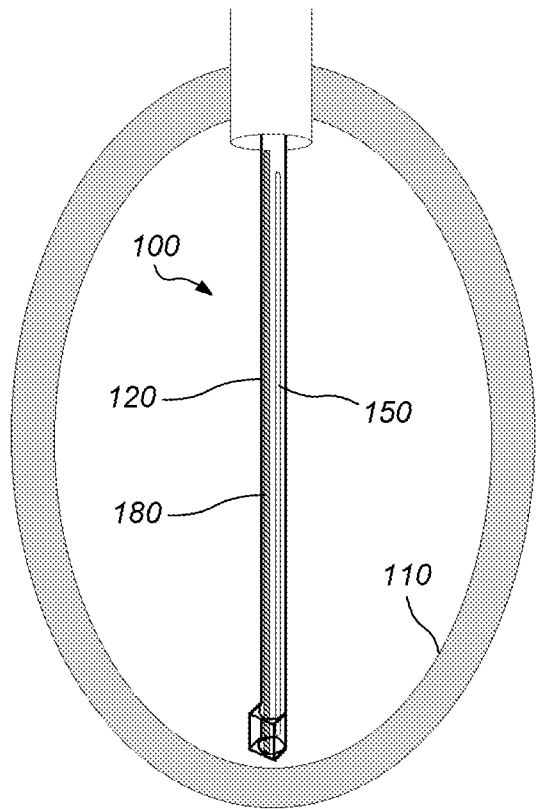
FIG. 2 depicts a diagram of a side view of an embodiment of a system for scoring human endocardium tissue as initially positioned through a conduit into a left ventricle.

In some embodiments, the system may include a second conduit positionable, during use, in the left ventricle of the human heart. The first conduit may be positionable, during use, in the second conduit. The first conduit (e.g., catheter) may be inserted into the left ventricle through a second conduit (e.g., FIG. 2, second conduit (e.g., guide catheter) shown as cylinder entering top of left ventricle). A guide wire may or may not be necessary, and if necessary, will be removed once the first conduit is in the left ventricle.

In some embodiments, a method may include ameliorating diastolic dysfunction of a human heart. In some embodiments, ameliorating diastolic dysfunction may include releasing elastic forces on the dysfunctional human heart. In some embodiments, ameliorating diastolic dysfunction may include cutting or scoring an endocardium of a left ventricle of the human heart. The endocardium tissue may be cut to a predetermined depth, in some embodiments, of about 5 mm to about 8 mm. The endocardium tissue may be cut to a predetermined depth, in some embodiments, of about 5% to about 50% of the thickness of a ventricular wall. The endocardium tissue may be cut through a depth of endocardium and at least a portion of a distance, in some embodiments, between a mitral valve and an apex of a left ventricle. The endocardial tissue may be cut about 50% to about 90% of a distance between a mitral valve and an apex of a left ventricle.

Figure 7E:
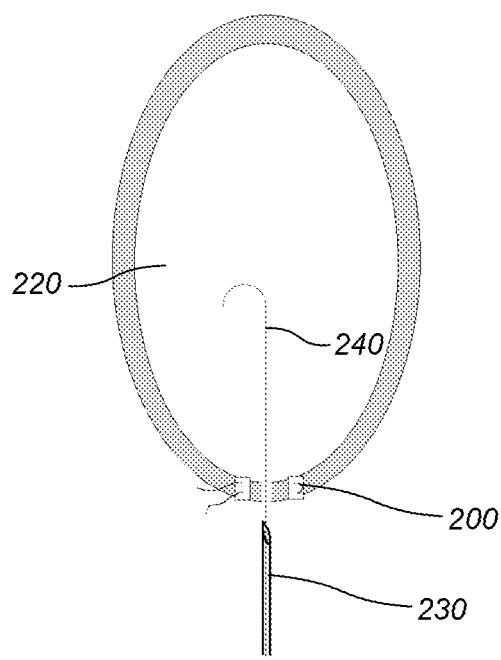
Figure 7F:
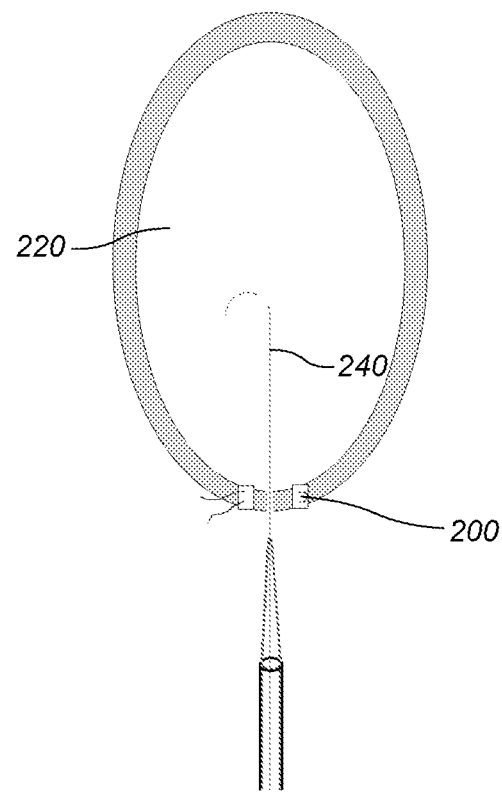
Figure 7G:
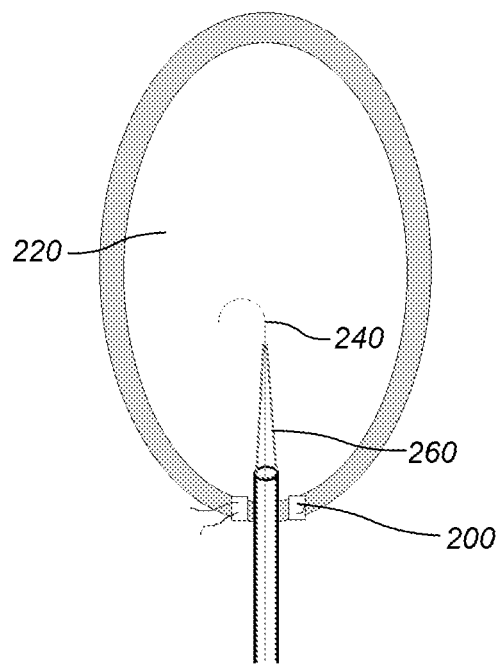
Figure 7H:
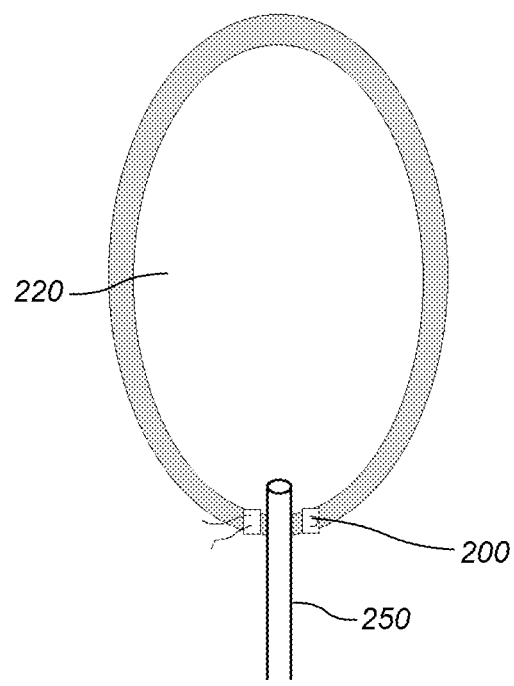

A left ventricle of a human heart may be accessed to accomplish procedures described herein using a number of different methods. In some embodiments, the left ventricle may be accessed through a valve (e.g., mitral valve) and/or an artery (e.g., femoral artery). In some embodiments, the left ventricle may be accessed directly through a ventricular wall of the heart. FIGS. 7A-H depict a diagram of a side view of an embodiment of a method for preparing a pathway for an instrument for scoring human endocardium tissue in a left ventricle. In some embodiments, a method may include preparing a site at an apex of the left ventricle of the human heart. Preparing a site may include suturing pledgets 200 to apex 210 of left ventricle 220 (e.g. as depicted in FIGS. 7A-B). The pledgets may be used to control any discharges occurring during the procedure. The method may include inserting needle 230 into left ventricle 220 between two or more of the pledgets (e.g. as depicted in FIG. 7C). Guide wire 240 may be passed through needle 230 into left ventricle 220 (e.g. as depicted in FIG. 7D). After insertion of the guide wire the needle may be removed while leaving the guide wire positioned in the left ventricle (e.g. as depicted in FIG. 7E). Second conduit 250 (e.g., a guide catheter) may be inserted in left ventricle 220 (e.g., along guide wire 240). In some embodiments, entry device 260 may be employed in order to facilitate entry of second conduit 250 into left ventricle 220 through the opening created by needle 230 (e.g. as depicted in FIGS. 7F-G). Upon insertion of the second conduit, the guide wire and the entry device may be removed (e.g. as depicted in FIG. 7H). In some embodiments, a method may include rapidly pacing the heart (e.g., 200-220 beats per minute) for a short period of time essentially resulting in the heart appearing motionless so that scoring may be facilitated. In some embodiments, a method may include pacing the heart more slowly such that the heart is not motionless, but beating at a controlled rate. This method may include automating the translation of a cutting device along the endocardium in coordination with the beat of the heart (i.e. in coordination with the pacing rate). This coordinated translation of the cutting device with the beat of the heart may facilitate the scoring of the endocardium by providing pressure between the endocardium and the cutting device as the heart contracts. In this method, the cutting device may be a serrated blade, and the contraction of the heart may create a sawing motion between the blade and the endocardium to facilitate the scoring.

Figure 8:
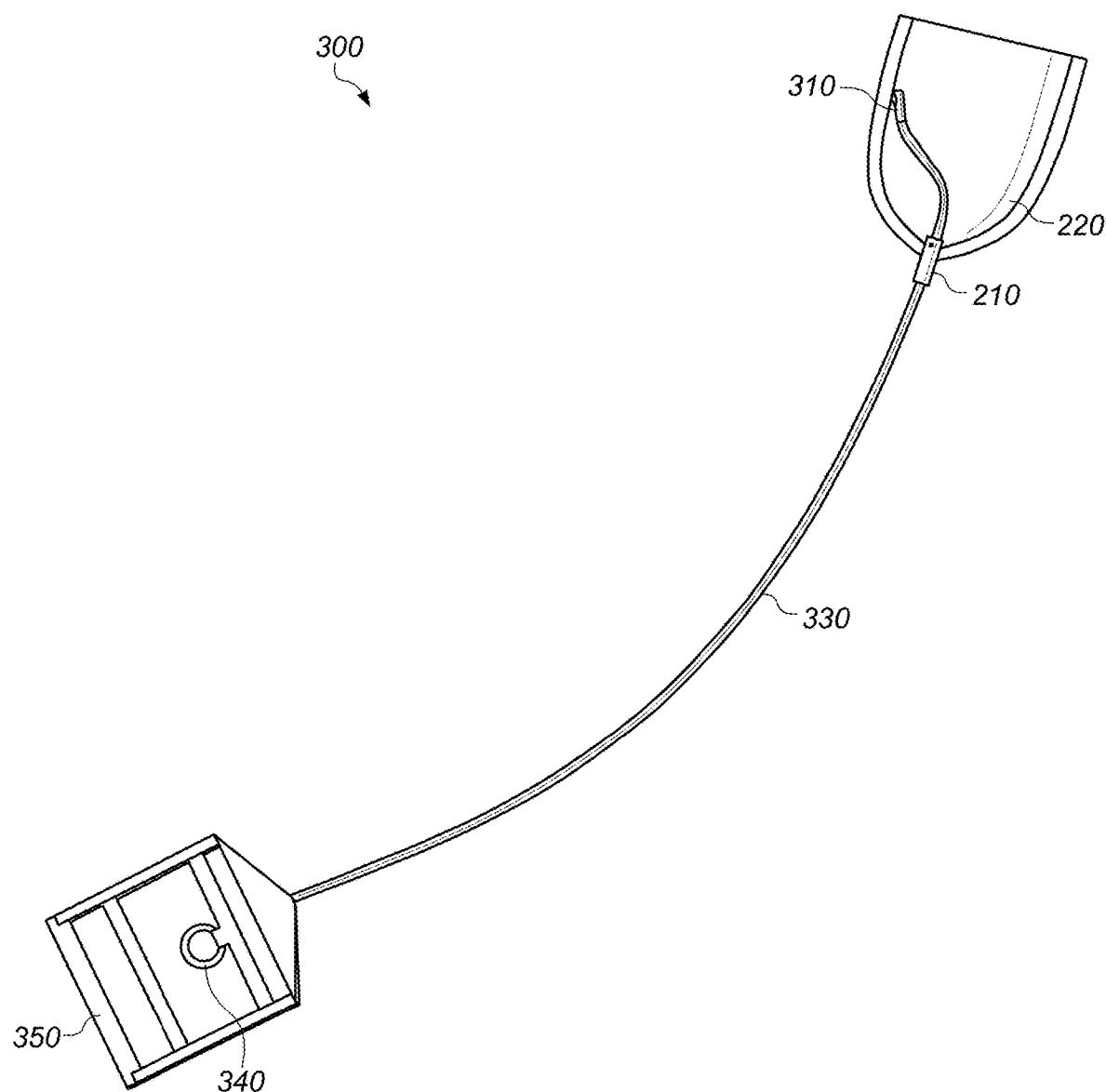
FIG. 8 depicts a diagram of a side view of an embodiment of a system for scoring human endocardium tissue in a left ventricle after insertion of a distal end of the system in the left ventricle.
Figure 9:
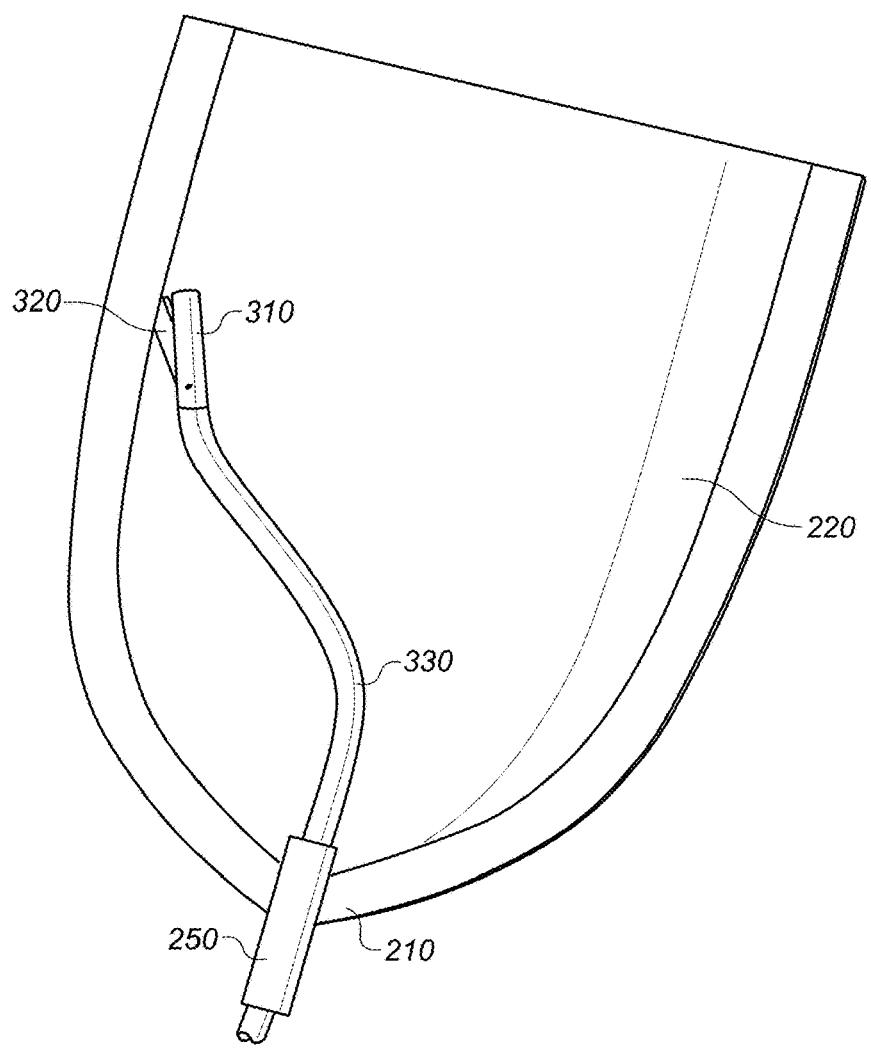
FIG. 9 depicts a diagram of a side view of an embodiment of a distal end of a system for scoring human endocardium tissue in a left ventricle after insertion of the distal end of the system in the left ventricle.
Figure 10:
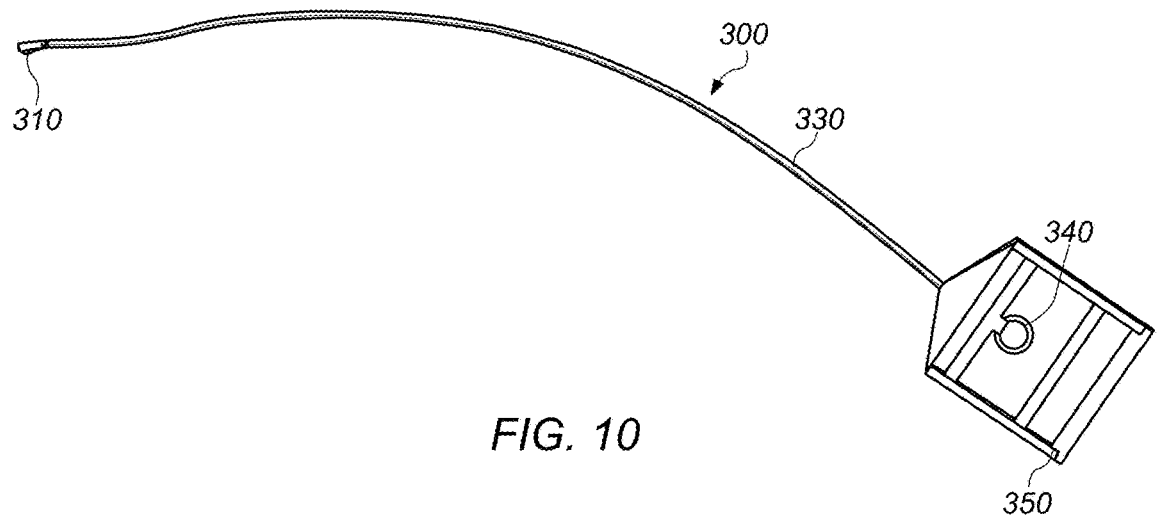
FIG. 10 depicts a diagram of a side view of an embodiment of a system for scoring human endocardium tissue in a left ventricle.
Figure 11:
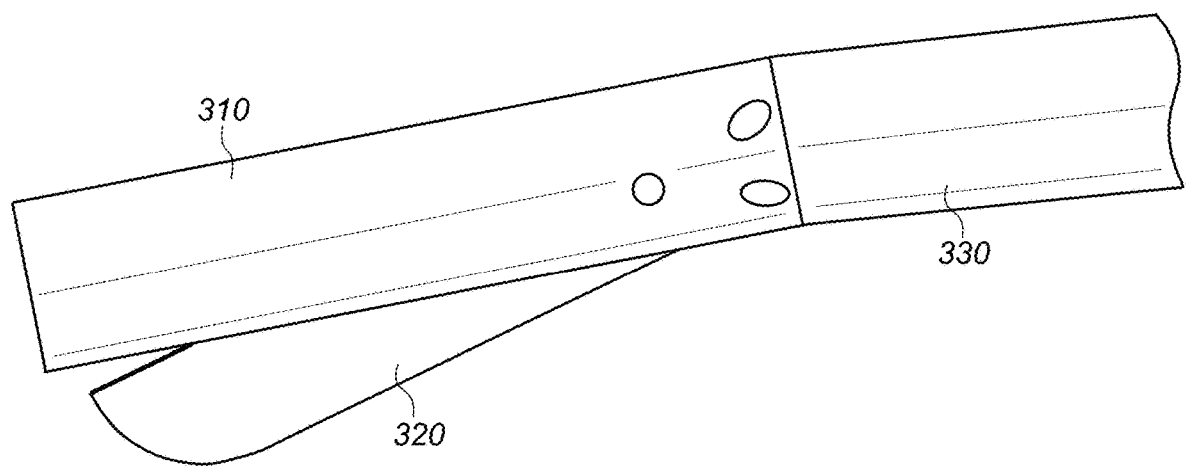
FIG. 11 depicts a diagram of a side view of an embodiment of a distal end of a system for scoring human endocardium tissue in a left ventricle.

In some embodiments, a system may be introduced (e.g., through second conduit 250) in a left ventricle to score an endocardium. FIGS. 8-11 depict a diagram of an embodiment of system 300 for scoring human endocardium tissue in left ventricle 220 after insertion of distal end 310 of the system in the left ventricle. System 300 may be inserted into left ventricle 220 through a second conduit. Cutting device 320 may be positionable in distal end 310. Cutting device 320 may extend out of distal end 310 (which may include a first conduit 330) upon activation of the cutting device during use. The cutting device may be activated and extended out of the distal end of the first conduit after being positioned in the left ventricle. Once cutting device 320 is engaged at the tissue surface, a user may draw system 300 down towards apex 210 (e.g. as depicted in FIGS. 8-9) and the second conduit 250 opening. At the end of the cut, the cutting device may be retracted and repositioned if additional cuts are desired.

The device may be inserted through the second conduit and into the left ventricular cavity. During the deployment through the second conduit the cutting device may be retracted. Once in the left ventricle, a user may deploy the blade to an adjustable depth of cut that will be set and locked in place using activation system 340.

In some embodiments, a medical imaging system (e.g., intra-cardiac echocardiography (ICE)) may be positioned to visualize the left ventricular wall. The imaging system may be used to assist in positioning the cutting device during use.

Positioning of the cutting device may include rotation. Rotation may be accomplished by rotating device handle 350 (e.g., theta control). Positioning the cutting blade against the interior ventricular wall may be set by pulling a tensioning mechanism in the device handle that will steer the distal end in at least one direction (e.g., z direction). The tensioning mechanism may withstand sufficient pressure to maintain position of the distal end while making a cut. In some embodiments, the tensioning mechanism may consist of a pulley device made of a material with enough tensile strength to maintain contact between the cutting blade and the endocardium. Such materials may include metal wire, carbon nanotubes, and similar materials.

In some embodiments, the system may include a shaping member positionable in the distal portion of the first conduit. The shaping member may substantially conform to a portion of a perimeter or endocardium of a left ventricle (e.g., control in the radial dimension). In some embodiments, the shaping member may be positioned in the distal end of the first conduit after the distal end has been positioned in the left ventricle facilitating appropriate positioning of the cutting device relative to the endocardium tissue. In some embodiments, the shaping member, when activated during use, changes from a first shape to a second shape. The first shape may be substantially straight and the second shape substantially conforms to a portion of a perimeter of a left ventricle. The shaping member may be activated after the distal end of the system is positioned in the left ventricle. The shaping member may be coupled along the distal portion of the first conduit. In some embodiments, a shaping member may include a plurality of members coupled to one another. The plurality of members may function to control a curvature of the distal end. The plurality of members may function to assist in controlling a shape of the distal end by allowing movement but only within certain predetermined parameters. The parameters of allowed movement imposed by the plurality of members may be adjusted by adjusting the shapes of the individual members and/or how they are connected.

In some embodiments, distal end steering may not be locked in place to allow tactile feedback to continuously modulate contact pressure of the cutting device against the left ventricular wall. Once the cutting device (e.g., blade) is engaged at the tissue surface, a user may draw the device down towards the apex and the second conduit opening. At the end of the cut, the cutting device may be retracted and repositioned if additional cuts are desired. Following the final cut the cutting device may be retracted into the first conduit at which point the device can be safely withdrawn through the second conduit.

Figures 12A, 12B:
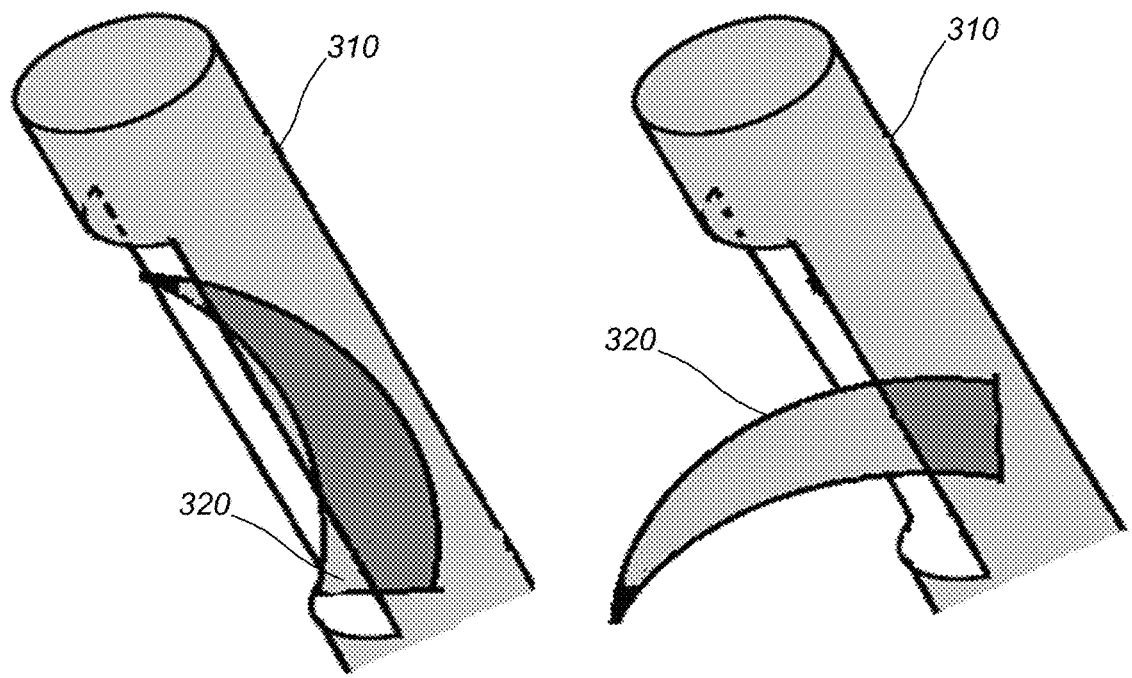
FIGS. 12A-B depict a diagram of a side view of an embodiment of a distal end of a system for scoring human endocardium tissue in a left ventricle comprising a curved blade.
Figures 13A, 13B, 13C, 13D, 13E, 13F:
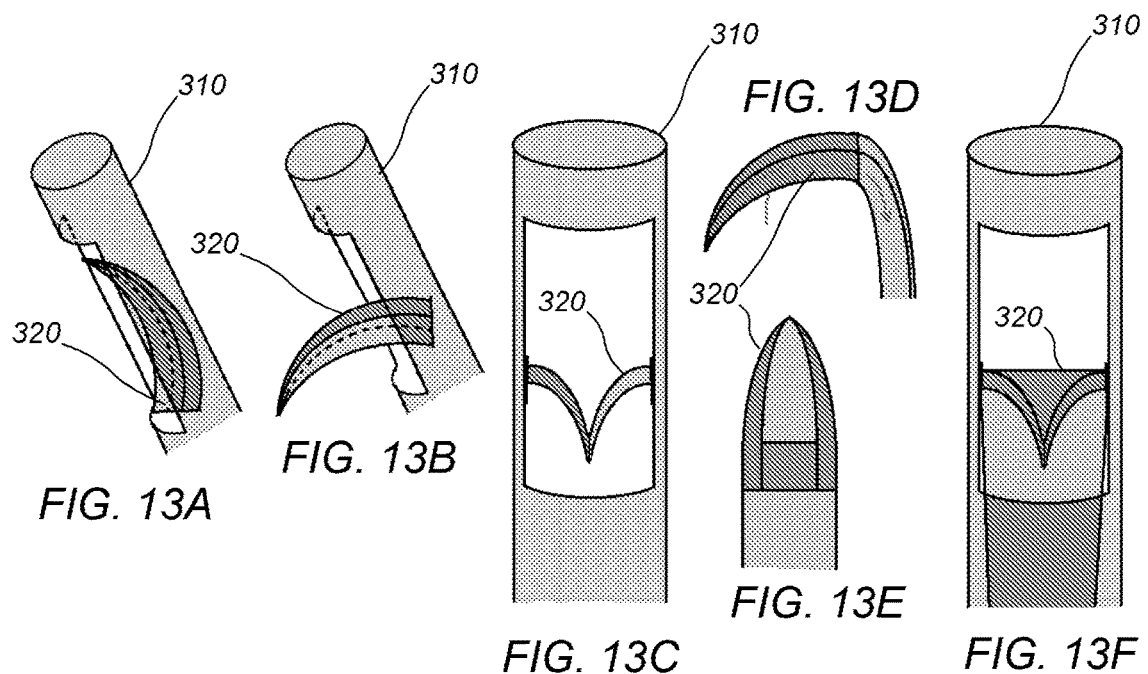
FIGS. 13A-F depict a diagram of a side view of an embodiment of a distal end of a system for scoring human endocardium tissue in a left ventricle comprising two curved blades.
Figures 14A, 14B, 14C, 14D:
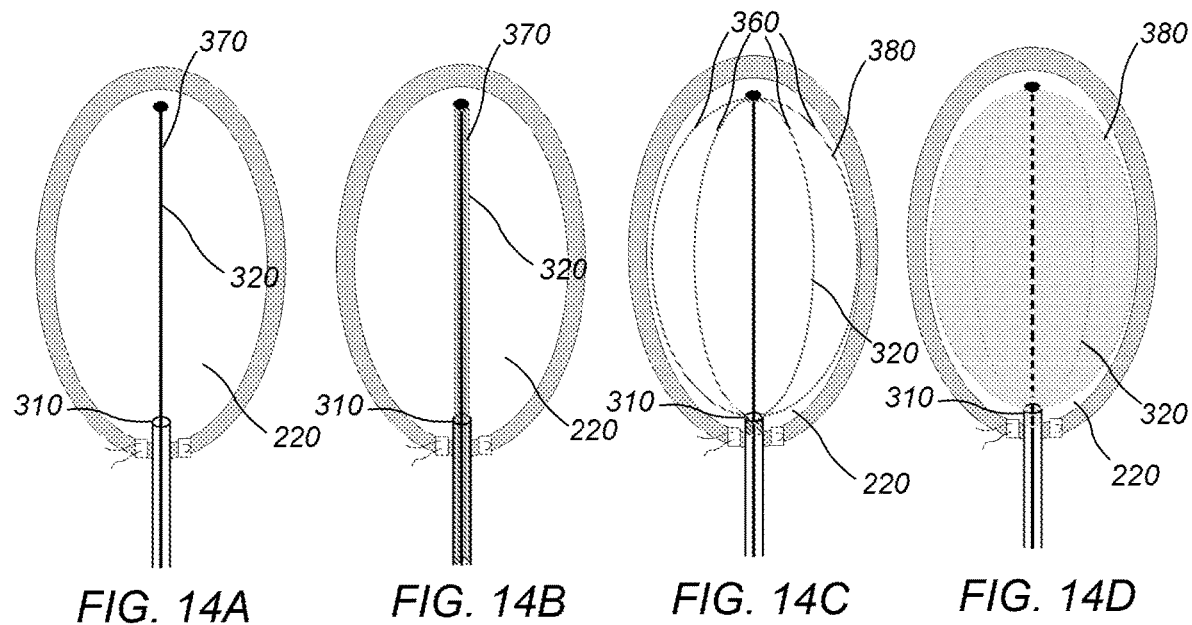
FIGS. 14A-D depict a diagram of a side view of an embodiment of a system for scoring human endocardium tissue in a left ventricle after insertion of a distal end of the system in the left ventricle, wherein the system may include an expanding form which fills and scores the endocardium tissue.
Figures 17A, 17B, 17C:
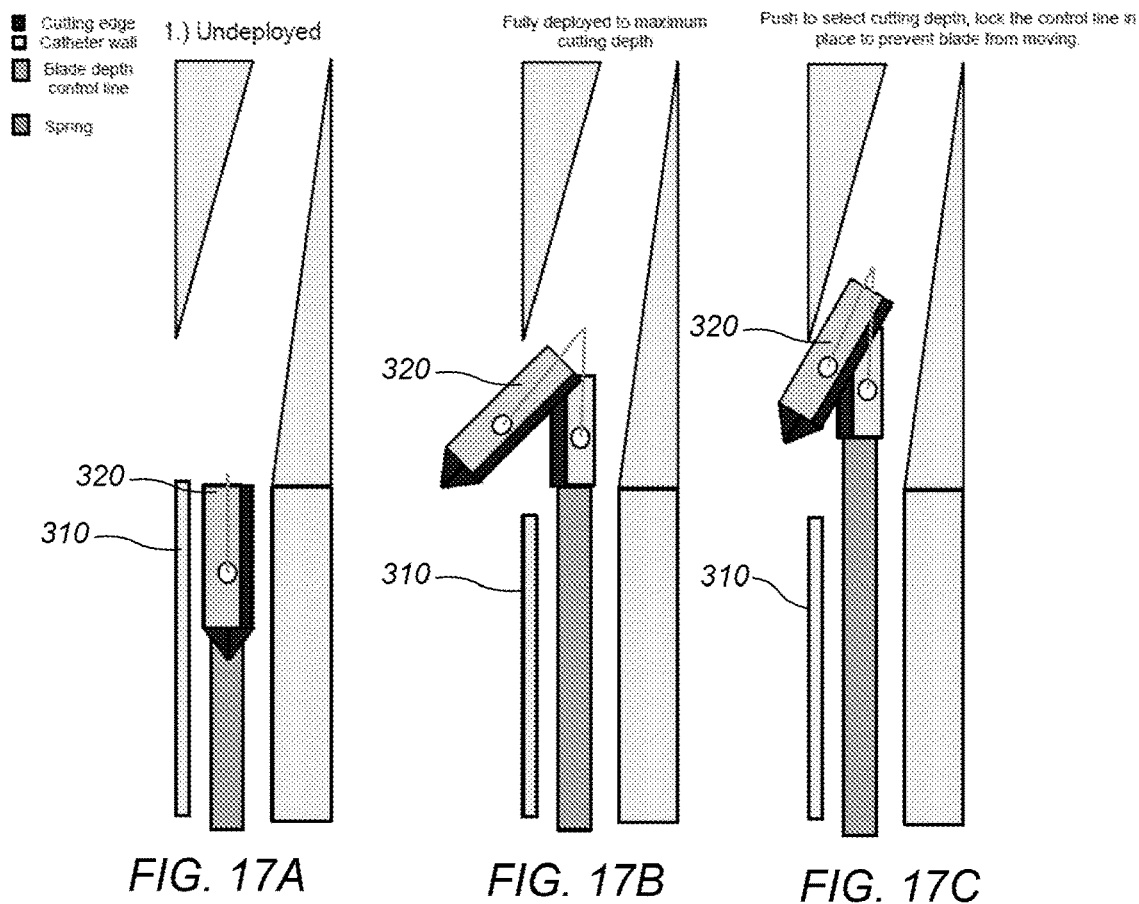
FIGS. 17A-C depict a diagram of a side view of an embodiment of a distal end of a system for scoring human endocardium tissue in a left ventricle comprising a straight blade

The design of the distal end and cutting device may include different embodiments. FIGS. 17A-C depict a diagram of a side view of an embodiment of distal end 310 of a system for scoring human endocardium tissue in a left ventricle comprising cutting device 320 (e.g., a straight blade) which may be initially retracted within the first conduit. This cutting device may be deployed to variable depth by variable advancement of a depth control line coupled to activation system 340. This deployment may be achieved by a spring mechanism. This blade may be retracted into the embodiment by further advancement of a depth control line for safe repositioning or removal of the cutting device from the left ventricle. FIGS. 12A-B depict a diagram of a side view of an embodiment of distal end 310 of a system for scoring human endocardium tissue in a left ventricle comprising curved blade 320. In some embodiments, the cutting device may include a hooked blade, a curved blade, or a straight blade. In some embodiments, the cutting device may include a serrated blade. The cutting device may include a blade including an arcuate shape (curved blade, e.g., as depicted in FIGS. 12A-B) in an orientation such that a distal end of the blade penetrates, during use, the endocardium tissue before any other portion of the blade In some embodiments, the deployment of the cutting surface may rotate out of a protective sheath, may protrude out of the distal end of a sheath, or the sheath may be retracted from around the cutting surface to expose a set depth for the cutting device.

In some embodiments, a cutting device may include a double hooked blade for cutting out a wedge of tissue rather than scoring. FIGS. 13A-F depict a diagram of a side view of an embodiment of distal end 310 of a system for scoring human endocardium tissue in a left ventricle comprising curved blade 320. The cutting device may include a "double hooked blade" or a blade comprising two arcuate blades such that a distal end of the blade includes a convergence of the arcuate blades. The blade may excise at least a portion of the endocardium during use, such that the blade gouges a portion of tissue out as opposed to simply cutting the tissue. This double hooked blade may also have a protective sheath which the blade may rotate out of to make the cuts.

In some embodiments, the top of the double blade may be covered and the bottom of the double blade may be open. The open bottom may direct any excised tissue toward the first conduit. In some embodiments, suction (e.g., using a pressure reduction system) may be applied to the opening via a flexible tube extending down the sheath to the handle of the system, to remove the excised tissue out of the body. The purpose of the double cutting blade is to prevent healing of the endocardial cut, so that the initial benefit of the operation is maintained long term.

There is concern that a single longitudinal cut may heal overtime. In some embodiments, anti-fibrotic medications (e.g., angiotensin converting enzyme inhibitors and angiotensin receptor blocking medications which are already FDA approved and prescribed in these same patients) may be used to prevent endocardial healing.

In some embodiments a system for scoring endocardium tissue may include an expanding device. FIGS. 14A-D depict a diagram of a side view of an embodiment of a system for scoring human endocardium tissue in left ventricle 220 after insertion of distal end 310 of the system in the left ventricle, wherein the system may include cutting device 320 including an expanding form which substantially fills the left ventricle and scores the endocardium tissue. The cutting device may be configurable to assume first shape 370 and second shape 380. The first collapsed shape may facilitate movement of the cutting device through the first conduit. The second expanded shape may be substantially equivalent to and/or fill an interior of a left ventricle. When the cutting device assumes the second shape in a left ventricle the cutting device cuts, during use, through at least a portion of a depth of endocardium tissue positioned adjacent the cutting device. The cutting device may include a plurality of flexible elongated members 360. At least a portion of at least one of the elongated members may include a cutting edge. In some embodiments, at least one of the elongated members comprises a blade which conveys, during use, along at least a portion of the at least one elongated member. The elongated members may be expanded using a mechanical mechanism. The elongated members may include a memory shape material (e.g., nitinol) which expands to the second shape when exposed to normal human temperatures (e.g. 37° C.). In some embodiments, the cutting device may include a balloon which expands from a deflated first shape to an inflated second shape. The expandable cutting device may score the tissue using blades attached to the wire or balloon which are stationary and produce the scoring due to pressure against the left ventricular wall. Scoring may be accomplished by electrocautery of the rails of the basket or attached to the balloon surface.

In some embodiments, a system for scoring human endocardium tissue may include a stabilizing device. The stabilizing device may apply, during use, a substantially opposing force on the epicardium substantially opposite the cutting device when the cutting device cuts through at least a portion of the depth of the endocardium tissue. The stabilizing device may be to buttress against on the epicardium or outside of the heart. Such a device may provide support for the endocardial scoring device. This may be accomplished using, for example, magnetism or a fixed forceps. FIGS. 15A-B depict a diagram of a side view of an embodiment of system 300 for scoring human endocardium tissue in left ventricle 220 after insertion of distal end 310 of the system in the left ventricle. The system may include stabilizing device 390 including a magnet which assists in guiding cutting device 320 during the scoring of the endocardium tissue. The stabilizing device may include magnetic properties and the cutting device may be ferromagnetic such that the stabilizing device guides the cutting device along the endocardium tissue. At least a portion of the stabilizing device may form channel 400 oriented, during use, towards the epicardium. The stabilizing device may include magnetic properties and the cutting device may be ferromagnetic such that the stabilizing device guides the cutting device along the endocardium tissue using the channel.

In some embodiments, the stabilizing device may be coupled to first elongated member 410. The first elongated member may be coupled to first conduit 420 such that an open portion of the channel is oriented towards a cutting portion of the cutting device. In some embodiments, the first elongated member may be coupled to the first conduit such that the stabilizing device and the cutting device are biased to be in close proximity to one another while allowing movement relative to one another.

FIG. 16 depicts a diagram of a side view of an embodiment of system 300 for scoring human endocardium tissue in left ventricle 220 after insertion of distal end 310 of the system in the left ventricle. The system may include stabilizing device 390 including a substantially fixed forceps mechanism which assists in guiding cutting device 320 during the scoring of the endocardium tissue. The stabilizing device is coupled to a first elongated member and the first elongated member is coupled to the cutting device at a point exterior, during use, to a heart forming pivot point 430 between the stabilizing device and the cutting device. In some embodiments, the pivot point may be positionable along either the first or second elongated member allowing a user to adjust a minimum attainable distance between the stabilizing device and the cutting device. In some embodiments, the stabilizing device comprises a plurality of deformations which increase, during use, a coefficient of friction between the stabilizing device and the epicardium.

In some embodiments, a method of ameliorating diastolic dysfunction may include positioning a second conduit in a human body such that a distal end of the second conduit is positioned in a left ventricle of a human heart. The method may include positioning a first conduit in the second conduit such that a distal end of the first conduit extends beyond the distal end of the second conduit into the left ventricle. The method may include activating a cutting device to sever at least one trabeculae carneae. Severing trabeculae carneae in a left ventricle of a human heart may release pressure on the heart. At least some of the trabeculae carneae may be severed adjacent an apex of the left ventricle.

EXAMPLES

Figure 18:
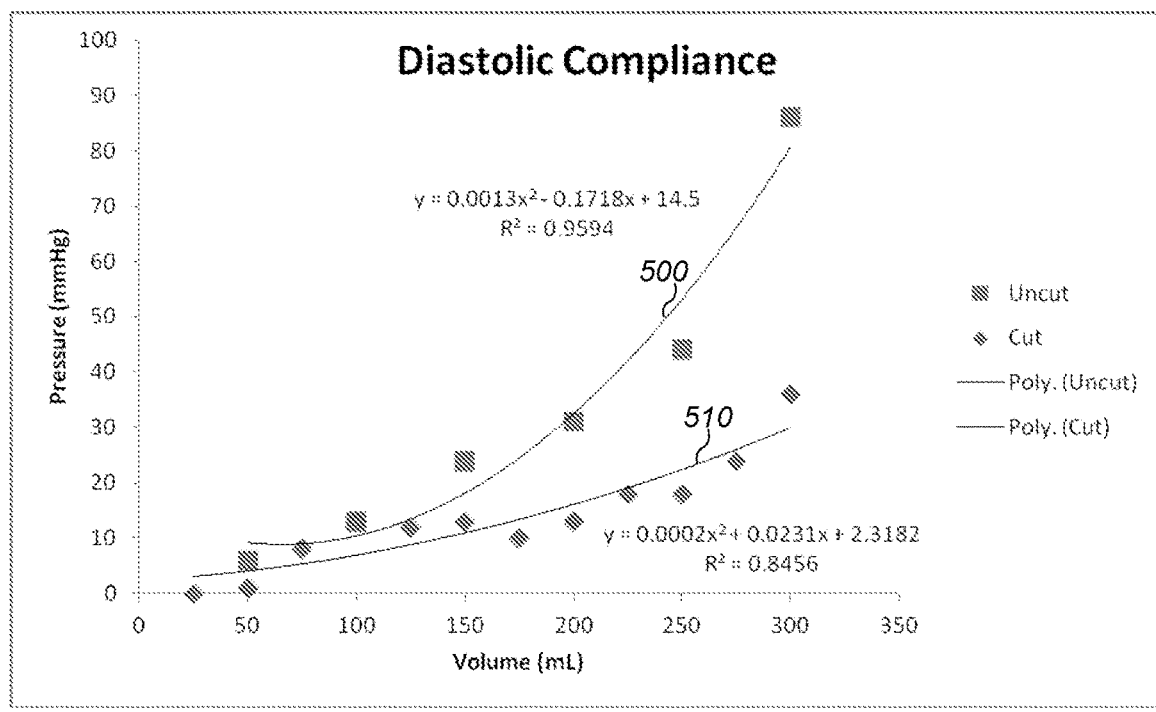
FIG. 18 depicts a graph of a case study wherein a system for scoring human endocardium tissue was used for increasing left ventricular compliance in a subject. The reduction to practice was performed using an ex vivo human heart with diastolic compliance measured with a balloon inserted into the left ventricular cavity to measure passive diastolic pressure-volume relations both before and immediately following scoring of the endocardium.
Figure 19:
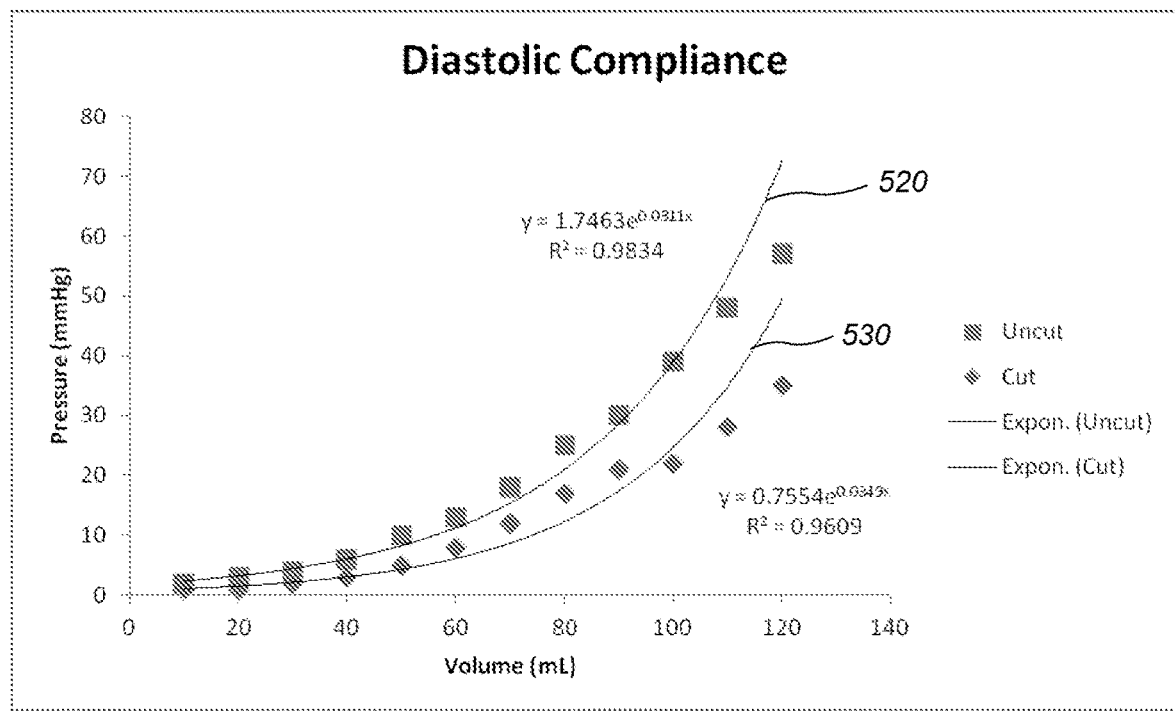
FIG. 19 depicts a graph of a case study wherein a system for scoring human endocardium tissue was used for increasing left ventricular compliance in a subject.
Figure 20:
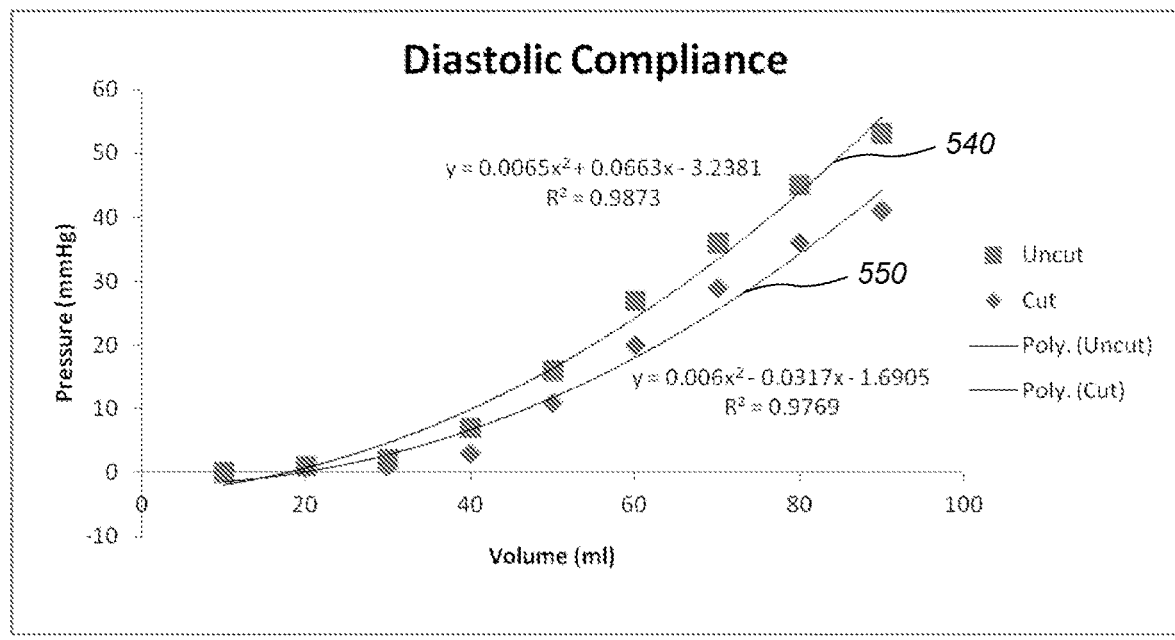
FIG. 20 depicts a graph of a case study wherein a system for scoring human endocardium tissue was used for increasing left ventricular compliance in a subject.
Figure 21:
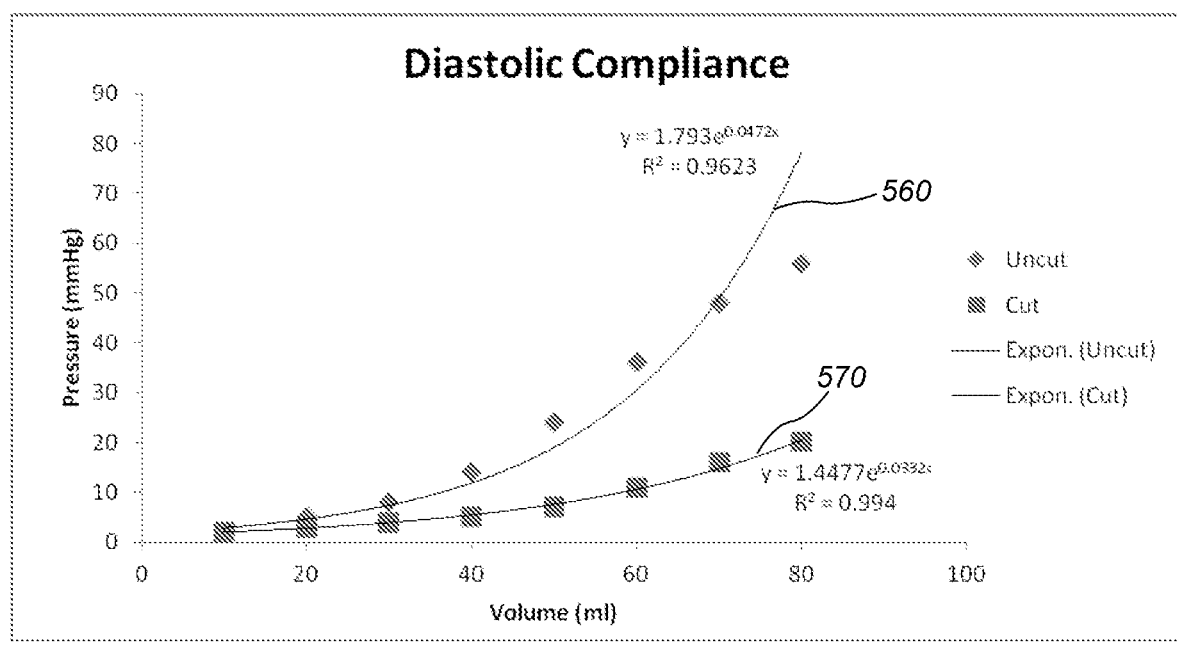
FIG. 21 depicts a graph of a case study wherein a system for scoring human endocardium tissue was used for increasing left ventricular compliance in a subject.

An isolated human heart was obtained and left ventricular diastolic compliance was measured at baseline, and following 4 longitudinal cuts extending from the left ventricular apex to the left ventricular base. FIG. 18 depicts a graph of a case study wherein a system for scoring human endocardium tissue was used for increasing left ventricular compliance in a subject. Prior to the procedure the patient had a dilated weak heart or systolic and diastolic dysfunction. The baseline data 500 is plotted relative to left ventricular diastolic compliance following scoring of the endocardium (510). As is visibly evident, there was a marked acute increase in left ventricular compliance demonstrating a successful reduction to practice of our approach. FIGS. 19-21 depicts a graph of a case study wherein a system for scoring human endocardium tissue was used for increasing left ventricular compliance in a subject. Prior to the procedure the patient had normal left ventricular systolic function and isolated diastolic dysfunction. The baseline data 520, 540, and 560 is plotted relative to left ventricular diastolic compliance following scoring of the endocardium (530, 550, and 570). As is visibly evident, there was a marked acute increase in left ventricular compliance demonstrating a successful reduction to practice of our approach.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of ameliorating diastolic dysfunction, comprising:
    positioning a second conduit in a human body such that a distal end of the second conduit is positioned in a left ventricle of a human heart;
    positioning a first conduit in the second conduit such that a distal end of the first conduit extends beyond the distal end of the second conduit into the left ventricle;

activating a cutting device to sever at least one trabeculae carneae while inhibiting damage to cardiac tissue directly attached to the severed trabeculae carneae; and releasing pressure on the human heart.

2. The method of claim 1, further comprising forming an opening in an apex of the left ventricle.

3. The method of claim 1, further comprising severing at least one trabeculae carneae adjacent an apex of the left ventricle.

4. The method of claim 1, wherein severing the at least one trabeculae releases at least some of the elastic forces on the left ventricle.

5. A method of ameliorating diastolic dysfunction, comprising:

positioning a second conduit in a human body such that a distal end of the second conduit is positioned in a left ventricle of a human heart;

positioning a first conduit in the second conduit such that a distal end of the first conduit extends beyond the distal end of the second conduit into the left ventricle;

activating a cutting device to sever at least one trabeculae carneae adjacent an apex of the left ventricle while inhibiting damage to cardiac tissue directly attached to the severed trabeculae carneae; and releasing at least some of the elastic forces on the left ventricle.

6. The method of claim 5, further comprising forming an opening in an apex of the left ventricle.

7. The method of claim 5, further comprising releasing pressure on the human heart.

8. A system for ameliorating diastolic dysfunction, comprising:

a first conduit, comprising:

a first opening positioned at a proximal end of the first conduit extending through the proximal end in communication with a first lumen extending through the first conduit;

a second opening extending from adjacent to a distal end portion of the first conduit;

a shaping member positionable in the distal portion of the first conduit, wherein the shaping member substantially conforms to a portion of a perimeter or endocardium of a left ventricle upon activation when exposed to elevated temperatures associated with the human body;

a cutting device positioned in the distal portion of the first conduit, wherein the cutting device, when activated, extends out of the second opening of the first conduit and severs, during use, at least one trabeculae carneae; and an activation system for activating the cutting device.

9. The system of claim 8, wherein activating the cutting device comprises retracting at least a portion of a sheath from a first position covering at least a portion of the second opening to a second position exposing the portion of the second opening.

10. The system of claim 8, wherein the cutting device comprises a blade.

11. The system of claim 8, wherein the cutting device comprises a serrated blade.

12. The system of claim 8, wherein the cutting device comprises a blade comprising an arcuate shape in an orientation such that a distal end of the blade penetrates.

13. The system of claim 8, wherein the shaping member, when activated during use, changes from a first shape to a second shape, wherein the first shape is substantially straight and the second shape substantially conforms to a portion of a perimeter or endocardium of a left ventricle.

14. The system of claim 8, wherein the shaping member, when activated during use, changes from a first shape to a second shape, wherein the first shape is substantially straight and the second shape substantially conforms to a portion of a perimeter or endocardium of a left ventricle.

* * * * *